United States Patent [19]

Kulmala et al.

[11] Patent Number: 5,663,452

[45] Date of Patent: Sep. 2, 1997

[54] PROCESS FOR THE PREPARATION OF 2-ETHYL-1,3-HEXANE DIOL

[75] Inventors: Kari Kulmala, Porvoo, Finland; Kjell Ankner, Mölnlycke, Sweden; Lea Rintala, Porvoo, Finland; Leila Lahtinen, Helsinki, Finland; Kalevi Heinola, Järvenpää, Finland

[73] Assignee: Neste OY, Espoo, Finland

[21] Appl. No.: 596,177

[22] PCT Filed: Sep. 2, 1994

[86] PCT No.: PCT/FI94/00387

§ 371 Date: May 3, 1996

§ 102(e) Date: May 3, 1996

[87] PCT Pub. No.: WO95/07254

PCT Pub. Date: Mar. 16, 1995

[30] Foreign Application Priority Data

Sep. 7, 1993 [FI] Finland ................... 933896

[51] Int. Cl.⁶ ........................... C07C 47/02
[52] U.S. Cl. .............. 568/461; 568/852; 568/388
[58] Field of Search .................. 568/852, 461

[56] References Cited

U.S. PATENT DOCUMENTS 4,215,076  7/1980  Stueben et al. ................ 568/461

FOREIGN PATENT DOCUMENTS 0367743  5/1990  European Pat. Off. .

OTHER PUBLICATIONS

Patent Abstracts of Japan, vol. 14, No. 86, C-690, JP-A-1-299240, Dec. 4, 1990.

Abstract of JP 2-040333, Dialog Inf. Services, Feb. 9, 1990.

*Primary Examiner*—C. Warren Ivy
*Assistant Examiner*—Sreeni Padmanabhan
*Attorney, Agent, or Firm*—Birch, Stewart, Kolasch & Birch, LLP

[57] ABSTRACT

The invention relates to a new, technically simple but efficient process, with a good yield, for the preparation of 2-ethyl-1,3-hexane diol from n-butyraldehyde by aldol condensation in the presence of an alkali metal hydroxide or alkali earth metal hydroxide catalyst. To promote the reaction and to improve its controllability, a neutral phase-transfer catalyst is additionally used in the process according to the invention. 2-Ethyl-1,3-hexane diol is used in insecticides and, for example, in the preparation of polyesters.

13 Claims, No Drawings

PROCESS FOR THE PREPARATION OF 2-ETHYL-1,3-HEXANE DIOL

This application is the U.S. National Phase application of PCT/FI94/00387 filed Sep. 2, 1994, published as WO95/07254 on 16 Mar. 1995.

The object of the invention is a new, technically simple but efficient process for the preparation of 2-ethyl-1,3-hexane diol from n-butyraldehyde by aldol condensation in the presence of an alkali metal hydroxide or an alkali earth metal hydroxide. The efficiency of the invention is based on the use of correctly selected catalyst combinations in the reaction.

2-ethyl-1,3-hexane diol is a compound known per se, which is a slightly oil-like, colorless liquid. 2-Ethyl-1,3-hexane diol is used in the main in insecticides, but it can also be used in the preparation of polyesters and in the paint industry as one component in the preparation of pulverous paints.

The preparation of 2-ethyl-1,3-hexane diol from n-butyraldehyde by aldol condensation in the presence of a catalytic amount of an alkali metal hydroxide or an alkali earth metal hydroxide and by subsequent hydrogenation (reduction) is known per se in organic chemistry. The hydrogenation of the intermediate can be carried out either by using reducing agents, e.g. sodium borohydride, or by catalytic hydrogenation.

JP patent publication 2 040 333 describes a process for the preparation of 2-ethyl-1,3-hexane diol by an aldol condensation reaction from n-butyraldehyde in a homogenous system in the presence of an alkali metal hydroxide and by reducing the formed 2-ethyl-3-hydroxyhexanal. n-Butyraldehyde and potassium hydroxide were allowed to react in butanol at 40° C., whereafter the intermediate formed with a yield of 50.4%, 2-ethyl-3-hydroxyhexanal, was hydrogenated by using Raney nickel at a temperature of 100° C. and a pressure of 50 atm for 1 h.

JP patent publication 1 299 240 discloses a process for the preparation of 2-ethyl-1,3-propane diol from n-butyraldehyde by aldol condensation by using alkali metal alkoxides as the catalyst. The reaction was performed in the presence of sodium methoxy in a butanol solution at 40° C. 2-Ethyl-3-hydroxyhexanal formed with a yield of 52.6%, and it was hydrogenated with Raney nickel at a temperature of 100° C. and a pressure of 50 atm.

The process according to the present invention is thus intended for the preparation of 2-ethyl-1,3-hexane diol by a technically simple but efficient process as the result of which a good yield of the end product is obtained. This objective presupposes that the course of the reaction can be controlled significantly better in the aldol condensation step, so that the amount of the hazardous byproduct, 2-ethyl-2-hexanal, formed even in the process according to the JP patent publication described above, can be decreased and thus the yield of the end product can be increased.

It has now been observed, surprisingly, that this objective is attained by correct selection of the catalyst combination used in the aldol condensation step of n-butyraldehyde. Thus the process according to the invention uses, in addition to an alkali metal hydroxide or alkali earth metal hydroxide catalyst, a neutral phase-transfer catalyst for promoting the reaction, whereby the course of the reaction can be rendered more controllable, i.e. the amount of the hazardous byproduct can be considerably decreased and thus the yield of the end product can be increased. The process according to the invention is thus characterized in what is stated in the characterizing clause of Claim 1. Such a combination of alkali metal hydroxide or alkali earth metal hydroxide catalysts and neutral phase-transfer catalysts is a novel and surprising technical solution for the preparation of 2-ethyl-1,3-hexane diol from n-butyraldehyde.

In the process according to the present invention, the preparation of 2-ethyl-1,3-hexane diol takes place in two steps, which are 1) an aldol condensation step and 2) hydrogenation. In step 1), a 2-ethyl-3-hydroxy-hexanal intermediate in accordance with Formula (II) is formed by aldol condensation from n-butyraldehyde (Formula I), and thereafter in step 2) the intermediate according to Formula (II) is hydrogenated by catalytic hydrogenation into 2-ethyl-1,3-hexane diol (Formula III). These steps can be described by using the following reaction formulae:

Step 1)

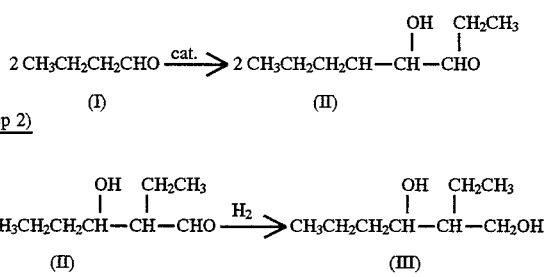

Step 2)

In the preparation process according to the invention it is very important that the hydroxy ions of the alkali metal hydroxide or alkali earth metal hydroxide catalysts can be transferred from the aqueous phase to the organic phase so that there will not form in the mixture even a local concentrated hydroxy-ion spot which would cause in the exothermal reaction too high a reaction temperature in consequence which water would crack from the desired intermediate according to Formula (II), 2-ethyl-3-hydroxy-hexanal, whereafter it would form 2-ethyl-2-hexenal according to Formula (IV), which is the worst byproduct of the reaction. 2-Ethyl-2-hexenal is further reduced in the hydrogenation step into 2-ethyl-hexanol according to Formula (V) and not into the desired 2-ethyl-1,3-hexane diol.

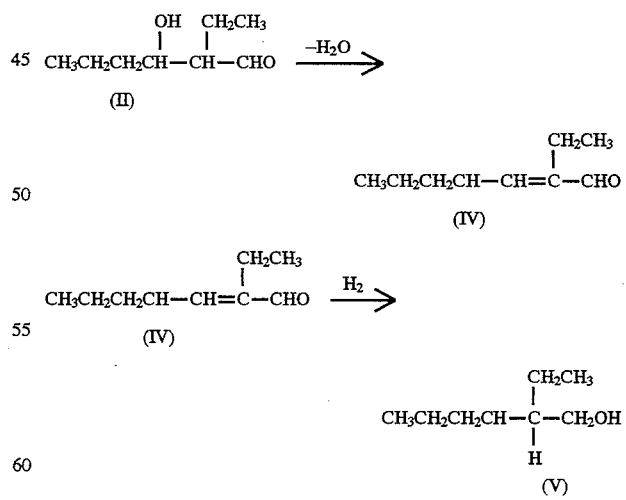

By using, in accordance with the present invention, in the aldol condensation step a neutral phase-transfer catalyst together with an alkali metal hydroxide or alkali earth metal hydroxide catalyst the amount of the non-desirable hexenal according to Formula (IV) is decreased to as low a level as below 2 percent, and the yield of the final product is increased to nearly 60 percent. These results can be deemed to be considerably better than the results obtained without a phase-transfer catalyst, as shown by the examples given below.

In a multiple-phase system, which is thus the type also of the preparation process disclosed in the present invention, it is possible to accelerate and promote the action of alkali metal hydroxide or alkali earth metal hydroxide catalysts either a) by carrying out the reaction in a homogenous system (usually homogenized by using short-chain alcohols) or b) by using chemical phase-transfer catalysts in a heterogenous system. Chemical phase-transfer catalysts are thus chemical compounds having the property of catalyzing inter-phase transfer of material. Phase-transfer catalysts may be cationic, anionic or neutral.

In the process according to the present invention, the interesting phases are the organic phase and the aqueous phase. It has now been observed that in this case an advantageous end result, i.e. efficiency, speed and controllability of the reaction, is achieved by using in the aldol condensation step of the initial-material aldehyde a neutral phase-transfer catalyst together with an alkali metal hydroxide or alkali earth metal hydroxide. Polyethylene glycol (PEG), for example, is a usable neutral phase-transfer catalyst.

Neutral phase-transfer catalysts do not have a charge as do, for example, cationic phase-transfer catalysts. The principle of action of a neutral phase-transfer catalyst between an organic phase and an aqueous phase can be described as follows, using polyethylene glycol as an example: Polyethylene glycol serves as a phase-transfer catalyst by attaching to a positive ion and by forming a so-called crown ether structure. The free electrons of the oxygen atoms of the polyethylene glycol attract the positive ions. The crown ether formed owing to the structure of the polyethylene glycol passes into the organic phase. To maintain the electron equilibrium in the phase, also the negative ions pass into the organic phase. When, for example, sodium hydroxide is used in the reaction, polyethylene glycol forms with $Na^+$ a crown ether, which passes into the organic phase, and the $OH^-$ ions follow to maintain the electron equilibrium. Since the reaction taking place in the organic phase consumes hydroxyl ions, the above cycle repeats to maintain the electron equilibrium.

The preparation of 2-ethyl-1,3-hexane diol thus takes place in two steps, as shown above in the reaction formulae. In the first reaction step, n-butyraldehyde reacts with itself, forming as the product of the aldol reaction an intermediate-product β-hydroxyaldehyde according to Formula II, i.e. 2-ethyl-3-hydroxy-hexanal. This intermediate-product β-hydroxy-aldehyde is hydrogenated (reduced) into the corresponding alcohol, i.e. into 2-ethyl-1,3-hexane diol according to Formula III. The efficiency, speed and controllability of the aldol step can thus be improved significantly by using an alkali metal hydroxide or alkali earth metal hydroxide catalyst together with a neutral phase-transfer catalyst. The use of this catalyst combination renders the control of the exothermal forming reaction of the intermediate-product β-aldehyde maximally efficient, and thus the amount of readily forming hazardous byproducts can be minimized. In step 2, the intermediate-product aldehyde is hydrogenated completely into the desired end-product alcohol either by using a reducing agent or by catalytic hydrogenation. By this procedure, the desired objective, i.e. the surprisingly high yield of 2-ethyl-1,3-hexane diol, is achieved.

According to the present invention, 2-ethyl-1,3-hexane diol is thus prepared from n-butyraldehyde. 0.5–10% by weight, preferably 5–15% by weight, of a neutral phase-transfer catalyst is added to n-butyraldehyde, one such catalyst being, for example, polyethylene glycol (PEG 400), whereafter the mixture is cooled to 0°–20° C. The reaction may also be started from room temperature, but preferably so that the mixture is first cooled. Most preferably the reaction mixture is cooled to a temperature of 5°–15° C., and thereafter an aqueous solution of an alkali metal hydroxide or alkali earth metal hydroxide catalyst is added to the mixture drop by drop at such a rate that the reaction clearly starts, i.e. the temperature of the mixture clearly rises from its original value. The alkali metal hydroxide or alkali earth metal hydroxide is used in a proportion of 0.01–5% by weight, preferably 0.1–1% by weight, to n-butyraldehyde. The adding of the aqueous solution of the catalyst is discontinued when the temperature of the mixture has risen to the range 25°–45° C., preferably, however, to the range 30°–40° C. After the discontinuation of the adding of the catalyst, the mixture is further stirred for 0–5 h, preferably 0.2–3 h, whereafter the organic phase and the aqueous phase are separated from each other. Before the separation of the phases the reaction mixture may be neutralized with a mineral acid or an organic acid. The organic phase is recovered, and it is hydrogenated by catalytic hydrogenation at a temperature of 30°–200° C. and a pressure of 5–100 bar, preferably at a temperature of 60°–140° C. and a pressure of 10–60 bar. The hydrogenation may be carried out by using, for example, a Raney nickel catalyst. After the hydrogenation the product is vacuum distilled. The boiling point of 2-ethyl-1,3-hexane diol is 100° C./6 mbar, and a yield of up to more than 55% is obtained. When the process according to the invention is used, the worst byproduct, 2-ethyl hexanol via 2-ethyl hexenal, is formed at maximum at a rate of 2.6%. The rest of the reaction mixture is unreacted n-butyraldehyde which has become reduced to 1-butanol.

If a neutral phase-transfer catalyst is not used in accordance with the invention in the reaction, the controllability of the reaction is considerably poorer and the 2-ethyl hexenal byproduct may form in an amount of up to tens of percent.

The process according to the invention described above for the preparation of 2-ethyl-1,3-hexane diol is a simple, reliable and efficient method, with a high yield, for the preparation of the said compound.

The following examples describe the preparation process according to the invention in greater detail. However, they are intended only to illustrate the invention, and they must not be deemed to limit the invention.

EXAMPLE 1

101.0 g of n-butyraldehyde and 5.0 g of polyethylene glycol (PEG 400) were placed in a reactor. The mixture was cooled to 11° C., and a total of 171.0 g of a 0.25% aqueous solution of NaOH was added to it at such a rate that the temperature of the mixture remained at 30°–32° C. After 2 hours the mixture was neutralized with hydrochloric acid, the phases were separated, and the organic phase was hydrogenated with Raney nickel at 100° C. and at a hydrogen pressure of 20 bar. The product was analyzed gas chromatographically. The 2-ethyl-1,3-hexane diol yield was 57.7 g, which corresponded to a yield of 56.9%. The worst byproduct, 2-ethyl hexanol, formed in an amount of 1.8%, and the unreacted n-butyraldehyde had become reduced to 1-butanol.

EXAMPLE 2

The reaction was carried out by a procedure corresponding to that in Example 1, except that the 0.25% aqueous solution of NaOH was used in an amount of 72.3 g, and after the temperature of the mixture had risen to 32° C., it was maintained at that temperature for 3 h. The neutralization and hydrogenation were carried out as in Example 1. The 2-ethyl-1,3-hexane diol yield was 56.3%. The worst byproduct, 2-ethyl hexanol, formed in an amount of 2.6%, and the unreacted n-butyraldehyde had become reduced to 1-butanol.

EXAMPLE 3

Comparative Example 100.2 g of n-butyraldehyde was cooled to 10° C., and 81.0 g of a 1.24% aqueous solution of NaOM was added so that the temperature of the mixture rose to 35° C. The mixture was stirred at this temperature for 2.5 h. The phases were separated, and the organic phase was hydrogenated with Raney nickel, at a temperature of 100° C. and a pressure of 40 bar. The product was analyzed gas chromatographically. The yield of 2-ethyl-1,3-hexane diol was 49.6%. 2-Ethyl hexanol formed in an amount of 10.0%, and the balance was 1-butanol.

EXAMPLE 4

Comparative Example

The reaction was carried out as in Example 3, except that the stirring was continued for 20 h instead of 2.5 h. After hydrogenation the products were analyzed gas chromatographically. The yield of 2-ethyl-1,3-hexane diol was only 17.4%, 2-ethyl hexanol formed in as high an amount as 58.9%, and the balance was 1-butanol.

What is claimed is:

1. A process for the preparation of 2-ethyl-1,3-hexane diol from n-butyraldehyde by aldol condensation in the presence of an alkali metal hydroxide or alkali earth metal hydroxide catalyst and by hydrogenation of the obtained intermediate product, wherein a neutral phase-transfer catalyst comprising a polyalkylene glycol is additionally used in the aldol condensation step in an amount of 0.5–10% by weight.

2. A process according to claim 1, wherein the neutral phase-transfer catalyst is used in an amount of 1–5% by weight, of the amount of n-butyraldehyde.

3. A process according to claim 1, wherein the neutral phase-transfer catalyst is polyethylene glycol.

4. A process according to claim 1, wherein the alkali metal hydroxide or alkali earth metal hydroxide catalyst is used in a proportion of 0.01–5% by weight, to the n-butyraldehyde.

5. A process according to claim 1, wherein the preparation process comprises the following steps:

1) the n-butyraldehyde is caused to react with itself in an aldol condensation reaction in the presence of an alkali metal hydroxide or alkali earth metal hydroxide catalyst and a neutral phase-transfer catalyst, in consequence of which a 2-ethyl-3-hydroxy-hexanal intermediate product is formed, and 2) the 2-ethyl-3-hydroxy-hexanal obtained from step 1) is hydrogenated by means of a reducing agent or by catalytic hydrogenation into 2-ethyl-1,3-hexane diol.

6. A process according to claim 5, wherein the hydrogenation is carried out by using a Raney nickel hydrogenation catalyst.

7. A process according to claim 1, wherein the yield obtained for 2-ethyl-1,3-propane diol is over 50%.

8. A process according to claim 2, characterized in that the yield obtained for 2-ethyl-1,3-propane diol is over 50%.

9. A process according to claim 3, characterized in that the yield obtained for 2-ethyl-1,3-propane diol is over 50%.

10. A process according to claim 4, characterized in that the yield obtained for 2-ethyl-1,3-propane diol is over 50%.

11. A process according to claim 5, characterized in that the yield obtained for 2-ethyl-1,3-propane diol is over 50%.

12. A process according to claim 6, characterized in that the yield obtained for 2-ethyl-1,3-propane diol is over 50%.

13. A process according to claim 4, wherein the alkali metal hydroxide or alkali earth metal hydroxide catalyst is used in a proportion of 0.1–1% by weight, to the n-butyraldehyde.

* * * * *